United States Patent [19]

Feldman et al.

[11] 4,112,930

[45] Sep. 12, 1978

[54] APPARATUS AND METHOD FOR ECG BASELINE SHIFT DETECTING

[75] Inventors: Charles L. Feldman; Mark Hubelbank, both of Sudbury, Mass.

[73] Assignee: Electronics for Medicine, Inc., Pleasantville, N.Y.

[21] Appl. No.: 754,538

[22] Filed: Dec. 27, 1976

[51] Int. Cl.$^2$ .............................................. A61B 5/04
[52] U.S. Cl. ............................................... 128/2.06 R
[58] Field of Search ...................... 128/2.06 A, 2.06 B, 128/2.06 E, 2.06 F, 2.06 G, 2.06 R, 2.06 V, 2.1 R, DIG. 4

[56] References Cited

U.S. PATENT DOCUMENTS

| 3,212,496 | 10/1965 | Preston | 128/2.06 R |
| 3,608,543 | 9/1971 | Longini et al. | 128/DIG. 4 |
| 3,868,947 | 3/1975 | Holsinger | 128/2.06 B |
| 3,903,874 | 9/1975 | Shakespeare | 128/2.06 A |

Primary Examiner—William E. Kamm
Attorney, Agent, or Firm—Charles Hieken

[57] ABSTRACT

In an electrocardiographic system there is a multielement electrode at each skin location for providing an ECG signal of negligible magnitude between elements because of the close spacing while the pair of elements are sufficiently separated so that the motion of one element is at least partially independent of the motion of the other; thus, events causing a baseline shift will also cause a difference in potential between the two elements of a multielement electrode. That difference is detected by logical circuitry to produce a signal indicating baseline shift.

7 Claims, 2 Drawing Figures

APPARATUS AND METHOD FOR ECG BASELINE SHIFT DETECTING

BACKGROUND OF THE INVENTION

The present invention relates in general to detecting the shift in the baseline in an electrocardiogram (ECG) and more particularly concerns a novel system using a multiple element electrode at a single measuring location with means for detecting potential differences between elements to reliably detect the occurrence of a baseline shift, thereby preventing automatic monitoring equipment from indicating an alarm condition about a patient being monitored when an alarm condition should not be indicated. The apparatus is relatively easy to fabricate and install, adds relatively little cost to the system and operates relatively reliably with little attention from maintenance personnel.

Automatic ECG monitoring systems, whether using simple rate alarms on a bedside monitor or more complex arrhythmia detectors, produce erroneous results at times because of the presence of a non-ECG artifact, consisting of a combination of high frequency "muscle noise" and lower frequency "baseline shift". The present invention is concerned with detecting baseline shift; that is, a shift in the average value of the ECG signal over a waveform portion.

The usual cause of "baseline shift" is physical manipulation of the electrodes or the skin and muscle underlying electrodes which may result from movement of an electrode, pressing of the surfaces as a result of patient movement, tugging upon the electrode lead and other causes. Good preparation of the skin surface to which the electrode is attached helps minimize baseline shift but does not eliminate it. As an example of one approach to dealing with this problem reference is made to U.S. Pat. No. 3,905,364 entitled ARTIFACT DETECTOR.

The prior art includes a number of patents on electrodes and multiple electrode systems. In the prior art multiple electrode systems, multiple electrodes or multi-element electrodes are used to derive better estimates of the signal or to provide flexibility. Some multiple electrode systems are used to achieve rapid applications in emergency situations.

Prior art artifact detecting systems exemplified by Cudahy U.S. Pat. No. 3,905,364, Horth U.S. Pat. No. 3,552,386 and Vandenberg U.S. Pat. No. 3,050,841 detect artifact signals by sensing changes in the received signal out of range of a predetermined expected normal ECG from the same pair of electrodes used to derive the desired ECG signal; that is, between an electrode at a first ground or common location and an electrode at an ungrounded or uncommon location.

Holsinger U.S. Pat. No. 3,868,947 describes a multiple electrode system for artifact compensation and assumes a common mode artifact signal on the center electrodes of spaced coaxial electrode pairs in contact with the skin at spaced points with the outer annular electrode of each pair connected together and to a common ground of a differential amplifier having a pair of inputs respectively connected to respective ones of the center electrodes in a pair. This approach is of limited utility in solving the problem of detecting baseline shift because the causes of baseline shift at the location of one pair of electrodes is not likely to produce the same baseline shift, if any, at a spaced pair of electrodes.

Accordingly, it is an important object of this invention to provide improved methods and means for detecting baseline shift in an ECG signal.

It is a further object of the invention to achieve the preceding object with apparatus that is relatively easy and inexpensive to fabricate and install while providing a relatively reliable indication of baseline shift with relatively little attention to the apparatus.

It is a further object of the invention to achieve one or more of the preceding objects while providing a useful signal.

It is a further object of the invention to achieve one or more of the preceding objects useful in automatic ECG monitoring systems helpful in avoiding erroneous alarm conditions.

SUMMARY OF THE INVENTION

According to the invention, there is an electrode means for connection to a surface location on a patient for providing a reference potential. Preferably, there are two pairs of insulatedly separated but closely spaced electrode means (i.e. multiple element electrodes) for connection to a second and third location of a patient surface spaced from each other by a distance significantly greater than the spacing between elements of the multiple element electrodes. Each multiple element electrode provides a potential relative to the potential on said first electrode representative of the ECG activity of the patient. Each multiple element electrode also provides a differential potential between its elements which is representative of a baseline shift in said ECG signal. Preferably, there is differential amplifying means having first and second input connected to one element in each of the multiple element electrodes for providing an ECG signal and a reference input connected to said first electrode. Preferably, there are two differential amplifying means each having first and second inputs connected to respective elements of a multiple element electrode for providing an artifact signal and a reference input connected to said first electrode. Logical circuit means may be provided for responding to the occurrence of an artifact signal for disabling the alarm indicating apparatus of an automatic monitoring system and/or compensating for the baseline shift of the ECG signal. Numerous other features, objects and advantages will become apparent from the following specification when read in connection with the accompanying drawing in which:

Figure 1:
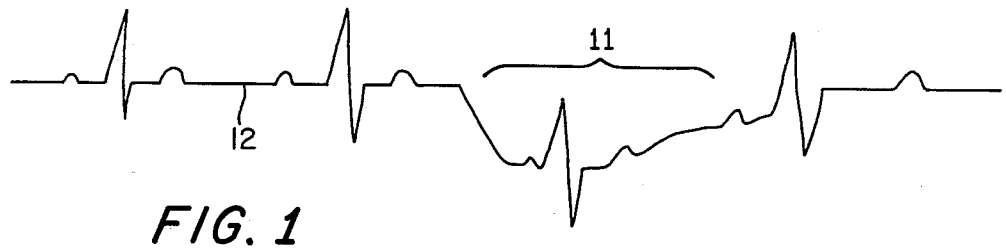
FIG. 1 is a graphical representation of an ECG signal indicating the occurrence of baseline shift.

With reference now to the drawing and more particularly FIG. 1 thereof, there is shown a graphical representation of an ECG signal with baseline shift occurring in the interval of the third illustrated beat 11 where the baseline shifts below the normal baseline level 12.

Figure 2:
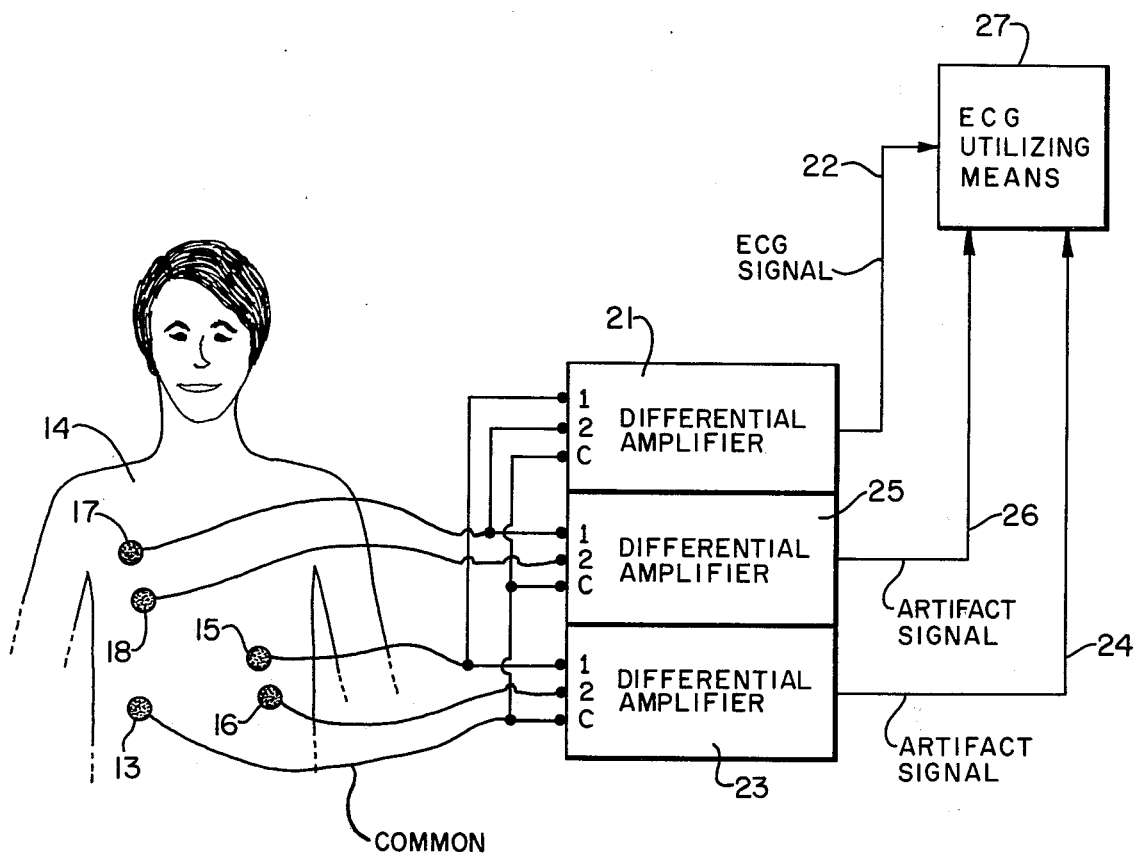
FIG. 2 is a combined block-diagram pictorial representation of an exemplary embodiment of a system according to the invention.

Referring to FIG. 2, there is shown a combined block pictorial representation of a system according to the invention for detecting baseline shift. The system includes a first ground, common or reference electrode 13 at a first surface location of patient 14 being monitored, a first pair of electrodes 15 and 16 at a second surface location of patient 14 and a second pair of electrodes 17 and 18 at a third surface location of patient 14. The spacing between electrodes 15 and 16 and between electrodes 17 and 18 is significantly less than the separation between the first location and each of the second and third locations and preferably that between the second and third locations. Typical separations between electrodes 17 and 18 and between electrodes 15 and 16 is one inch or less, and they are preferably arranged so that a line connecting their centers is perpendicular to the electrical axis of the heart. The separation between electrodes in a pair is small enough so that the ECG potential between them is negligible and large enough so that the motion of one electrode is at least partially independent of the motion of the other. The pairs of electrodes may be concentric as shown in Holsinger U.S. Pat. No. 3,868,947; however, the connection to external amplifying apparatus is different and as described below.

The system includes an ECG differential amplifier 21 for providing an ECG signal on line 22, a first artifact differential amplifier 23 for providing a first artifact signal on line 24 and a second artifact differential amplifier 25 for providing a second artifact signal on line 26. ECG utilizing means 27 receives the signals on lines 22, 24 and 26 and typically provides an alarm signal only when the ECG signal characterizes an unstable condition of patient 14, such as arrhythmia or an unacceptable heartbeat rate, while preventing the occurrence of an alarm signal when an artifact signal on lines 24 or 26 occurs signifying that a condition has occurred at an associated pair of electrodes producing a baseline shift.

The grounded, common or reference input C of each differential amplifier is connected to reference terminal 13 at the first patient surface location. It is common practice to have a reference terminal such as 13 attached to the patient and connected to one or more common terminals of the amplifying means for reducing noise. The 1 and 2 signal inputs of differential amplifier 23 are connected to electrodes 15 and 16, respectively, at the second patient surface location. The 1 and 2 signal inputs of differential amplifier 23 are connected to electrodes 15 and 16, respectively, at the second patient surface location. The 1 and 2 signal inputs of differential amplifier 25 are connected to electrodes 17 and 18, respectively, at the third patient surface location. The 1 signal input of ECG differential amplifier 21 is connected to electrode 15 at the second location. The 2 input of ECG differential amplifier 21 is connected to electrode 17 at the third location. The ECG signal on line 22 is thus representative of the potential difference between the second and third patient surface locations.

The specific means for utilizing the ECG signal and the artifact signals is not a part of the invention. For example, the ECG utilizing means 27 may include logical or circuitry that responds to the occurrence of an artifact signal on either lines 24 or 26 for providing a signal that inhibits the alarm indicating circuitry. The ECG utilizing means might also or alternatively include circuitry for combining the artifact signals with the ECG signal to effectively restore the shifted baseline substantially to the normal baseline level 12.

There has been described novel apparatus and techniques for detecting a baseline shift in an ECG signal. It is evident that those skilled in the art may now make numerous modifications and uses of and departures from the specific embodiment described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Apparatus for providing an ECG signal and detecting baseline shift in said ECG signal comprising,
   at least a first multielement electrode means having elements closely spaced but insulatedly separated electrode means for connection to a first surface portion of a patient for providing a first ECG potential and also for providing therebetween a signal representative of baseline shift while the ECG potential therebetween is negligible,
   first means for differentially combining the potentials on said elements of said first electrode means to provide a first artifact signal representative of a baseline shift in said first ECG potential,
   at least another electrode means for contacting a second surface of said patient for providing a second ECG potential different from said first ECG potential,
   and second means for differentially combining said first and second ECG potentials to provide an ECG signal.

2. Apparatus for providing an ECG signal and detecting baseline shift in accordance with claim 1 wherein said another electrode means comprises,
   a second multielement electrode means for contacting said second surface portion of said patient with elements separated from each other by a distance significantly less than the distance between said first and second multielement electrode means.

3. Apparatus for providing an ECG signal and detecting baseline shift in an ECG signal in accordance with claim 2 and further comprising,
   third means for differentially combining the potentials on said elements of said second electrode means to provide a second artifact signal representative of a baseline shift in said second ECG potential.

4. Apparatus for providing an ECG signal and detecting baseline shift in an ECG signal in accordance with claim 3 and further comprising a third electrode means at a third surface portion of said patient wherein each of said differential amplifying means includes a common input connected to said third electrode means.

5. Apparatus for providing an ECG signal and detecting baseline shift in an ECG signal in accordance with claim 1 wherein the spacing between said elements is less than one inch.

6. Apparatus for providing an ECG signal and detecting baseline shift in an ECG signal in accordance with claim 1 and further comprising a third electrode means at a third surface portion of said patient wherein said each of said differential amplifying means includes a common input connected to said third electrode means.

7. A method of providing providing an ECG signal and detecting baseline shift in said ECG signal which method includes the steps of,
   positioning first and second closely spaced but insulatedly separated electrode portions in contact with a first surface portion of a patient positioned so that in the absence of baseline shift the ECG potential therebetween is negligible, there being substantially a first ECG potential on both said electrode portions,
   differentially combining the potential on said electrode portions to provide a first artifact signal representative of a baseline shift in said first ECG potential, contacting a second surface of said patient with another electrode means to provide a second ECG potential different from said first ECG potential, and differentially combining said first and second ECG potentials to provide an ECG signal.

* * * * *